United States Patent
Ito et al.

(10) Patent No.: US 6,881,565 B2
(45) Date of Patent: Apr. 19, 2005

(54) PROTEIN HAVING GLUTAMINASE ACTIVITY AND GENE ENCODING THE SAME

(75) Inventors: Kotaro Ito, Noda (JP); Tetsuya Oguma, Noda (JP); Yasuji Koyama, Noda (JP)

(73) Assignee: Kokkoman Corporation, Noda (JP)

( * ) Notice: Subject to any disclaimer, the term of this patent is extended or adjusted under 35 U.S.C. 154(b) by 256 days.

(21) Appl. No.: 10/123,116

(22) Filed: Apr. 17, 2002

(65) Prior Publication Data

US 2003/0124656 A1 Jul. 3, 2003

(30) Foreign Application Priority Data

Apr. 20, 2001 (JP) ........................................ 2001-121845

(51) Int. Cl.[7] ............................. C12N 9/78; C12N 15/55
(52) U.S. Cl. ..................................... 435/227; 536/23.2
(58) Field of Search ............................. 435/227, 252.3; 536/23.2

(56) References Cited

U.S. PATENT DOCUMENTS

| | | | | |
|---|---|---|---|---|
| 3,717,470 A | * | 2/1973 | Yokotsuka et al. | 426/51 |
| 3,852,479 A | * | 12/1974 | Yokotsuka et al. | 426/44 |
| 3,912,822 A | * | 10/1975 | Yokotsuka et al. | 426/44 |
| 4,684,527 A | * | 8/1987 | Motai et al. | 426/46 |
| 6,036,983 A | * | 3/2000 | Nielsen | 426/53 |
| 6,063,409 A | * | 5/2000 | Sato et al. | 426/52 |

* cited by examiner

*Primary Examiner*—Charles L. Patterson, Jr.
(74) *Attorney, Agent, or Firm*—Birch, Stewart, Kolasch & Birch, LLP

(57) ABSTRACT

There are disclosed a protein having an amino acid sequence shown in SEQ ID NO:2, or a protein having a glutaminase activity in which one or more amino acids is/are deleted from, substituted by, inserted to or added to the amino acid sequence of the above protein; a gene containing DNA encoding the above protein or a gene which hybridizes with the a complementary sequence of DNA of the above gene under a stringent condition and encodes a protein having a glutaminase activity; a recombinant DNA containing the above gene; a transformant or a transductant containing the above recombinant DNA; and a process for producing glutaminase which comprises culturing the above transformant or the above transductant and collecting glutaminase from a culture medium.

2 Claims, No Drawings

SEQUENCE LISTING

<160> NUMBER OF SEQ ID NOS: 13

<210> SEQ ID NO 1
<211> LENGTH: 2103
<212> TYPE: DNA
<213> ORGANISM: Cryptococcus albidus

<400> SEQUENCE: 1

```
atgtctctcc ttcgccttgc gctccttgcc tccttgaccg caactaccct cgctgcagga      60
cccgctggca atgaagacta ccagttccaa tctcgaagtc gtctgcgatc cctgtcgact     120
atcaataaat tctccgctcg agacaacctg gccccagtca gcctttcact cgaccaaaca     180
tcgtacacct tcagcgttca agatgagtcg gaggacaagg tctacattc cccggccggg      240 gataaattca aaaagtatac cctgaccgcc aacgggctag catctttgaa gcatgagatt     300
tcagcgtctg tgatgccaat gaccgttttc gaagtgacgg gccagcaaca gctgacctgt     360
gacagcatgg ggaaggccgt agccgattac ttggctacag acgatgtctg gaacgaggcg     420
ttcatgcaga ctattcttct taagtcggac aagcccatca gctttgcggc cgaccttcat     480
gaatgtcttc ctggacattg gggaacctcc gtggtgctta gcaccgctca aacccagggc     540
aatttgcagg gcattaacgt gaagaccgtc tctgcaaaga ctgtgccctc cggaccatac     600
atagcctctt acaaccacgc cagcgactcg atcgatctga ctcaagtatt ccgactttac     660
cgggaccaag aacaggcatt cacgaccccc ctgatcccct tcgctgatgg acaaagcttt     720
tcgccgctcg ccgcacaagt gtccggcatg aacaccatat ctattcctgt accttcgcgc     780
```

```
ctgtacacca agaacgtcgc gaatcctaga gcgctcgagg gagttcgagt cgctgtcaag    840
gatctgtatg atgtcgctgg cgtgccgagt ggattgggaa accgagccta ctggctaacc    900
tatgagccga gaaacgttac ggctgtttct attcaacgcc tgattgacca gggtgccgtc    960
atcataggca aagtgaagac ttcgcaattt gcaaacggtg aaacaccaac agcggactgg   1020
caagatcaac tcagtccttt caacatgcga ggcgacggct accaggatcc ttccacctca   1080
tcagccggca gtggttccag tatcggcgcc tacgactggg tagacgtgac tatcggttct   1140
gacaccggcg gctcggttcg tgaccccgct gccaacaacg gcgctttcgg tattcgacct   1200
tcgcacggcc ccatctccct tgagggcgtc atgccaatga gtgcgccgtt agacacggct   1260
ggttacttga cacggaacgc caaggagttt gcagcgttcg ggaaagcttg gtatggggac   1320
aagtttgagt cctacaacga aagcccaag accatctttg tccccaacga ctacttcccg   1380
ctcgcatcgg acgcgaaccc cgctgcgcaa ccgatctacg acgatttcat cgaatctctg   1440
cagtcgtatc tgaatgcctc catcgacaca cggtcctttg ccgacatttg gaactcgagc   1500
ggaaccatgg agcaggtcca acagactatc ccgtccttcc tgaacgaaac atacctact   1560
ttgattgggt actaccaatg gacgaacttc ggtcagccct ggttcgagga ctacgcctcc   1620
cgacacgatg gccgaactcc ctttatcgat tcgacccctg ctgttcgttg gcatatggt    1680
cgacagaggg gagaggctgg ttttgaagag gaactgcgaa ggaagaatgt gttccgggat   1740
ttcttttcgg aatacgtgtt gaaggcggac aacgagactt gcaccgatgc gttgttcttg   1800
tacccccatca acaccggttt cacgtcctac cgaaacggat acaaggccgc gcccctgcct   1860
ccattcggcg tcttcaacga agtctattcg cccttccacg aaggccccga aatctctatt   1920
ccactcggac aagttccgta caattccacc gtcagcaacc acgtcgagta cttgcccgtc   1980
agtgtcgcca tcagcgctcg gccaggctgc gattacgtct tgctcgatct cgctgcaggt   2040
cttcaggatg ctggaatcat ttccgccacg gagaccggct ctttgaccta tccttttgaag  2100
tag                                                                  2103
```

<210> SEQ ID NO 2
<211> LENGTH: 700
<212> TYPE: PRT
<213> ORGANISM: Cryptococcus albidus

<400> SEQUENCE: 2

```
Met Ser Leu Leu Arg Leu Ala Leu Leu Ala Ser Leu Thr Ala Thr
  1               5                  10                  15

Thr Leu Ala Ala Gly Pro Ala Gly Asn Glu Asp Tyr Gln Phe Gln
                 20                  25                  30

Ser Arg Ser Arg Leu Arg Ser Leu Ser Thr Ile Asn Lys Phe Ser
                 35                  40                  45

Ala Arg Asp Asn Leu Ala Pro Val Ser Leu Ser Leu Asp Gln Thr
                 50                  55                  60

Ser Tyr Thr Phe Ser Val Gln Asp Glu Ser Glu Asp Lys Val Tyr
                 65                  70                  75

Ile Ser Pro Ala Gly Asp Lys Phe Lys Lys Tyr Thr Leu Thr Ala
                 80                  85                  90

Asn Gly Leu Ala Ser Leu Lys His Glu Ile Ser Ala Ser Val Met
                 95                 100                 105

Pro Met Thr Val Phe Glu Val Thr Gly Gln Gln Gln Leu Thr Cys
                110                 115                 120

Asp Ser Met Gly Lys Ala Val Ala Asp Tyr Leu Ala Thr Asp Asp
```

-continued

```
                125                 130                 135
Val Trp Asn Glu Ala Phe Met Gln Thr Ile Leu Leu Lys Ser Asp
            140                 145                 150
Lys Pro Ile Ser Phe Ala Ala Asp Leu His Glu Cys Leu Pro Gly
            155                 160                 165
His Trp Gly Thr Ser Val Val Leu Ser Thr Ala Gln Thr Gln Gly
            170                 175                 180
Asn Leu Gln Gly Ile Asn Val Lys Thr Val Ser Ala Lys Thr Val
            185                 190                 195
Pro Ser Gly Pro Tyr Ile Ala Ser Tyr Asn His Ala Ser Asp Ser
            200                 205                 210
Ile Asp Leu Thr Gln Val Phe Arg Leu Tyr Arg Asp Gln Glu Gln
            215                 220                 225
Ala Phe Thr Thr Pro Leu Ile Pro Phe Ala Asp Gly Gln Ser Phe
            230                 235                 240
Ser Pro Leu Ala Ala Gln Val Ser Gly Met Asn Thr Ile Ser Ile
            245                 250                 255
Pro Val Pro Ser Arg Leu Tyr Thr Lys Asn Val Ala Asn Pro Arg
            260                 265                 270
Ala Leu Glu Gly Val Arg Val Ala Val Lys Asp Leu Tyr Asp Val
            275                 280                 285
Ala Gly Val Pro Ser Gly Leu Gly Asn Arg Ala Tyr Trp Leu Thr
            290                 295                 300
Tyr Glu Pro Arg Asn Val Thr Ala Val Ser Ile Gln Arg Leu Ile
            305                 310                 315
Asp Gln Gly Ala Val Ile Ile Gly Lys Val Lys Thr Ser Gln Phe
            320                 325                 330
Ala Asn Gly Glu Thr Pro Thr Ala Asp Trp Gln Asp Gln Leu Ser
            335                 340                 345
Pro Phe Asn Met Arg Gly Asp Gly Tyr Gln Asp Pro Ser Thr Ser
            350                 355                 360
Ser Ala Gly Ser Gly Ser Ser Ile Gly Ala Tyr Asp Trp Val Asp
            365                 370                 375
Val Thr Ile Gly Ser Asp Thr Gly Gly Ser Val Arg Asp Pro Ala
            380                 385                 390
Ala Asn Asn Gly Ala Phe Gly Ile Arg Pro Ser His Gly Ala Ile
            395                 400                 405
Ser Leu Glu Gly Val Met Pro Met Ser Ala Pro Leu Asp Thr Ala
            410                 415                 420
Gly Tyr Leu Thr Arg Asn Ala Lys Glu Phe Ala Ala Phe Gly Lys
            425                 430                 435
Ala Trp Tyr Gly Asp Lys Phe Glu Ser Tyr Asn Glu Arg Pro Lys
            440                 445                 450
Thr Ile Phe Val Pro Asn Asp Tyr Phe Pro Leu Ala Ser Asp Ala
            455                 460                 465
Asn Pro Ala Ala Gln Pro Ile Tyr Asp Asp Phe Ile Glu Ser Leu
            470                 475                 480
Gln Ser Tyr Leu Asn Ala Ser Ile Asp Thr Arg Ser Phe Ala Asp
            485                 490                 495
Ile Trp Asn Ser Ser Gly Thr Met Glu Gln Val Gln Thr Ile
            500                 505                 510
Pro Ser Phe Leu Asn Glu Thr Tyr Pro Thr Leu Ile Gly Tyr Tyr
            515                 520                 525
```

```
Gln Trp Thr Asn Phe Gly Gln Pro Trp Phe Glu Asp Tyr Ala Ser
                530                 535                 540

Arg His Asp Gly Arg Thr Pro Phe Ile Asp Ser Thr Pro Ala Val
            545                 550                 555

Arg Trp Ala Tyr Gly Arg Gln Arg Gly Glu Ala Gly Phe Glu Glu
            560                 565                 570

Glu Leu Arg Arg Lys Asn Val Phe Arg Asp Phe Phe Ser Glu Tyr
            575                 580                 585

Val Leu Lys Ala Asp Asn Glu Thr Cys Thr Asp Ala Leu Phe Leu
            590                 595                 600

Tyr Pro Ile Asn Thr Gly Phe Thr Ser Tyr Arg Asn Gly Tyr Lys
            605                 610                 615

Ala Ala Pro Leu Pro Pro Phe Gly Val Phe Asn Glu Val Tyr Ser
            620                 625                 630

Pro Phe His Glu Gly Pro Glu Ile Ser Ile Pro Leu Gly Gln Val
            635                 640                 645

Pro Tyr Asn Ser Thr Val Ser Asn His Val Glu Tyr Leu Pro Val
            650                 655                 660

Ser Val Ala Ile Ser Ala Arg Pro Gly Cys Asp Tyr Val Leu Leu
            665                 670                 675

Asp Leu Ala Ala Gly Leu Gln Asp Ala Gly Ile Ile Ser Ala Thr
            680                 685                 690

Glu Thr Gly Ser Leu Thr Tyr Pro Leu Lys
            695                 700

<210> SEQ ID NO 3
<211> LENGTH: 22
<212> TYPE: PRT
<213> ORGANISM: Cryptococcus albidus

<400> SEQUENCE: 3

Lys His Glu Ile Ser Ala Ser Val Met Pro Met Gly Val Phe Glu
  1               5                  10                  15

Val Thr Gly Gln Gln Gln Leu
                20

<210> SEQ ID NO 4
<211> LENGTH: 21
<212> TYPE: PRT
<213> ORGANISM: Cryptococcus albidus

<400> SEQUENCE: 4

Thr Val Ser Ala Lys Thr Val Pro Ser Gly Pro Tyr Ile Ala Ser
  1               5                  10                  15

Tyr Asn His Ala Ser Asp
                20

<210> SEQ ID NO 5
<211> LENGTH: 25
<212> TYPE: PRT
<213> ORGANISM: Cryptococcus albidus

<400> SEQUENCE: 5

Asn Val Ala Asn Pro Arg Ala Leu Glu Gly Val Arg Val Ala Val
  1               5                  10                  15

Lys Asp Leu Tyr Asp Val Ala Gly Val Pro
                20                  25
```

-continued

<210> SEQ ID NO 6
<211> LENGTH: 26
<212> TYPE: DNA
<213> ORGANISM: Artificial Sequence
<220> FEATURE:
<223> OTHER INFORMATION: Synthetic oligonucleotide primer derived from
      Cryptococcus albidus
<220> FEATURE:
<221> NAME/KEY: misc_feature
<222> LOCATION: (1)..(26)
<223> OTHER INFORMATION: any n = inosine

<400> SEQUENCE: 6
gtnatgccna tgggngtntt ygargg                                    26

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide primer derived from
      Cryptococcus albidus
<220> FEATURE:
<221> NAME/KEY: misc_feature
<222> LOCATION: (1)..(23)
<223> OTHER INFORMATION: any n = inosine

<400> SEQUENCE: 7
tayathgcnw sntayaayca ygc                                       23

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide primer derived from
      Cryptococcus albidus
<220> FEATURE:
<221> NAME/KEY: misc_feature
<222> LOCATION: (1)..(23)
<223> OTHER INFORMATION: any n = inosine

<400> SEQUENCE: 8
tgrttrtans wngcdtarta ngg                                       23

<210> SEQ ID NO 9
<211> LENGTH: 26
<212> TYPE: DNA
<213> ORGANISM: Artificial Sequence
<220> FEATURE:
<223> OTHER INFORMATION: Synthetic oligonucleotide primer derived from
      Cryptococcus albidus
<220> FEATURE:
<221> NAME/KEY: misc_feature
<222> LOCATION: (1)..(26)
<223> OTHER INFORMATION: any n = inosine

<400> SEQUENCE: 9
acnccytcna rngcnckngg rttngc                                    26

<210> SEQ ID NO 10
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 10
ttcttggtgt acaggcgcga aggtacagg                                 29

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 11
cgactcgatc gatctgactc aagtattcc                29

<210> SEQ ID NO 12
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 12
tctcggtacc atgtctctcc ttcgccttgc g              31

<210> SEQ ID NO 13
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 13
agagaattct ctacttcaaa ggataggtc                29

PROTEIN HAVING GLUTAMINASE ACTIVITY AND GENE ENCODING THE SAME

BACKGROUND OF THE INVENTION

1. Field of the Invention

The present invention relates to glutaminase and a glutaminase gene encoding the same, more specifically, to a protein having a glutaminase activity and excellent in salt tolerance and thermostability, and a gene encoding the protein having a glutaminase activity.

2. Prior Art

Glutaminase is an enzyme which generates ammonia and L-glutamic acid which gives good taste by hydrolyzing L-glutamine. Glutaminase has an important role in a food industry and is useful for producing, for example, soy sauce or flavoring foods obtained by enzymatically hydrolyzing protein. Glutaminase has been isolated from various kinds of biological species and its enzymological properties and the gene have been reported (e.g., Japanese Patent Publication No. 38748/1994).

In the preparation of soy sauce and the preparation of flavoring foods containing a large amount of salt, glutaminase excellent in an optimum pH, salt tolerance and thermostability has been desired. A group to which the present inventors have belonged has previously found a novel glutaminase which is excellent in salt tolerance and thermostability, and can effectively produce a protein-hydrolyzed product (e.g., soy sauce) enriched in an amount of glutamic acid from *Cryptococcus albidus* ATCC20293 (Journal of Japan Soy Sauce Research Institute, Vol.13, No.5, 1987, pp. 205–210, herein incorporated by reference).

For further improving the property of the above enzyme by a genetic engineering means and for producing the enzyme in a large amount, it is important to obtain a gene of the enzyme.

According to the above, it is possible to improve qualities of the protein-hydrolyzed product (e.g., soy sauce) easily and provide the same inexpensively.

SUMMARY OF THE INVENTION

An object of the present invention is to provide a protein having a glutaminase activity and excellent in salt tolerance and thermostability, and a gene encoding the same.

The present inventors have earnestly investigated about the above-mentioned problems in various manners and as a result, they have succeeded in isolating a glutaminase gene derived from *Cryptococcus albidus* to accomplish the present invention.

That is, the present invention provides the following materials and process.

1. A protein shown in either one of the following (a) and (b):
   (a) a protein having an amino acid sequence shown in SEQ ID NO:2,
   (b) a protein comprising an amino acid sequence in which one or more amino acids is/are deleted from, substituted by, inserted to or added to the amino acid sequence of the above-mentioned (a), wherein the protein has a glutaminase activity.
2. A gene comprising DNA shown in either one of the following (c) to (e):
   (c) a gene comprising DNA encoding the protein according to the above section 1,
   (d) a gene which hybridizes with a complementary sequence of the DNA of the above-mentioned (d) under a stringent condition and encodes a protein having a glutaminase activity, and
   (e) a gene encoding a protein comprising a base sequence having homology of 70% or more to the base sequence represented by the base numbers 1 to 2100 of SEQ ID NO:1 shown in the sequence listing and having a glutaminase activity.
3. A recombinant DNA containing the gene described in the above 2.
4. A transformant or a transductant containing the recombinant DNA described in the above 3.
5. A process for producing glutaminase which comprises culturing the transformant or the transductant described in the above 4 and collecting glutaminase from a culture medium.

DESCRIPTION OF THE PREFERRED EMBODIMENTS

In the following, the present invention will be explained in detail.

1. A Protein Having a Glutaminase Activity and a Gene Encoding the Same

The protein of the present invention is a protein shown in either of the following (a) or (b).
(a) a protein having an amino acid sequence represented by amino acid numbers 1 to 700 shown in SEQ ID NO:2,
(b) a protein comprising an amino acid sequence in which one or more amino acids is/are deleted from, substituted by, inserted to or added to the amino acid sequence of the above-mentioned (a), wherein the protein has a glutaminase activity.

The protein shown in (a) can be obtained by cloning a natural type glutaminase gene derived from a chromosomal DNA or cDNA of *Cryptococcus albidus* ATCC20293 and introducing the resulting clone into a suitable host-vector system to express the same.

Incidentally, the protein may be a mutant type in which one or a plural number of the amino acids is/are deleted from, substituted by, inserted into or added to the amino acid sequence of the above (a) so long as it has a glutaminase activity, as shown in the above (b). In the present specification, "a plural number" generally means 2 to 300, preferably 2 to 170, more preferably 2 to 50, most preferably 2 to 10 amino acids whereas it is different depending on a position in a steric structure or a kind of the amino acid residue.

Such a mutant type glutaminase, i.e., the protein of the above (b) can be obtained by introducing variation such as substitution, deletion, insertion, addition or inversion into the base sequence of the natural type glutaminase gene to prepare a variant type glutaminase gene, and introducing the gene into a suitable host-vector system to express the same.

As a method of introducing variation into a gene, there may be mentioned, for example, a site-specific mutation introducing method, a random mutation introducing method by PCR, and a method in which a gene is selectively cleaved and then a selected nucleotide is removed or added, and the cleaved genes are linked.

The glutaminase gene of the present invention is a gene containing DNA encoding the protein of the above (a) or (b). Incidentally, the glutaminase gene of the present invention may be a gene encoding a protein having a glutaminase activity which hybridizes with a complementary sequence of the DNA encoding the protein of the above-mentioned (a) or (b) under a stringent condition. In the present specification, "a stringent condition" means, for example, a condition wherein a sodium concentration is 50 to 300 mM, preferably about 150 mM and a temperature is 42 to 68° C., preferably about 65° C. Specific examples of the stringent condition may include, for example, a stringent condition in which hybridization is carried out by using 5×SSC, 1.0% (W/V) blocking agent for nucleic acid hybridization (available from Boehringer Manheim), 0.1% (W/V) N-lauroylsarcosine and 0.02% (W/V) SDS for overnight (about 8 to 16 hours) and washing is carried out by using 0.5×SSC, 0.1% (W/V) SDS, preferably 0.1×SSC, 0.1% (W/V) SDS for 15 minutes twice. Temperatures of the hybridization and washing are each 52° C. or higher, preferably 57° C. or higher, more preferably 62° C. or higher, most preferably 67° C. or higher.

As the DNA obtained under the stringent conditions, there may be exemplified by a gene encoding a protein comprising a base sequence having homology of 70% or more to the base sequence represented by the base numbers 1 to 2100 of SEQ ID NO:1 shown in the sequence listing and having a glutaminase activity. Homology is preferably 85% or more, more preferably 95% or more.

Examples of the gene containing DNA encoding the protein of the above-mentioned (a) may include DNA containing base sequence represented by the base numbers 1 to 2100 shown in SEQ ID NO:1 in the sequence listing. This DNA is a natural type glutaminase gene.

The natural type glutaminase gene can be obtained by cloning a natural type gene derived from a chromosomal DNA or cDNA of *Cryptococcus albidus* ATCC20293. As a method of cloning of the gene, for example, there may be mentioned a method in which glutaminase is purified and a partial amino acid sequence is determined, then, a suitable probe DNA is synthesized and screening is carried out from the chromosomal DNA of *Cryptococcus albidus* by using the probe DNA. Also, there may be mentioned a method in which a suitable primer DNA is prepared based on a partial amino acid sequence, and the DNA containing a fragment of the gene is amplified by a polymerase chain reaction (hereinafter abbreviated to as "PCR method") such as the 5' RACE method and the 3' RACE method, and the resulting DNAs are linked to obtain DNA containing a whole gene.

In more detail, a natural type glutaminase gene can be obtained as mentioned below. First, *Cryptococcus albidus* is cultured, and after the resulting culture broth is lyophilized in a liquid nitrogen, it is physically ground by using a mortar, etc., to obtain fine powder state cell pieces, and chromosomal DNA is extracted from the cell pieces by the conventional manner. In the extraction operation, a commercially available DNA kit can be utilized.

Then, glutaminase is purified to determine the N-terminal amino acid sequence. Further, an internal amino acid sequence may be determined. This can be obtained by determining an amino acid sequence of a peptide fragment obtained by digestion using lysylendopeptidase.

Glutaminase can be purified by using the partly modified method as disclosed in Japanese Provisional Patent Publication No. 332553/1999. That is, *Cryptococcus albidus* ATCC20293 is firstly inoculated into a suitable medium to obtain a culture broth containing proliferated cells. After adding a cell wall lytic enzyme to the cells obtained by centrifugation of the culture broth, the mixture was centrifuged to obtain a supernatant. The supernatant is heated to denature impurity proteins and the resulting material is further centrifuged to remove denatured proteins. To the above-mentioned supernatant is added ammonium sulfate for salting out, and centrifugation separation is carried out to remove insoluble proteins, thereby a crude enzyme solution containing glutaminase is obtained.

From the crude enzyme solution, a fraction(s) having glutaminase activity is/are purified by using a phenyl-Sepharose column, a DEAE-Sepharose column, a gel filtration column, an HPLC (high performance liquid chromatography), etc., whereby glutaminase can be purified.

Then, a primer to be used for PCR is synthesized in view of an information about a partial amino acid sequence, a codon use frequency of microorganisms belonging to *Cryptococcus* genus, and the like. Next, PCR is carried out using these primers and the chromosomal DNA obtained above as templates, whereby a DNA fragment encoding a part of glutaminase is obtained. Moreover, based on the base sequence of the resulting DNA, a primer is synthesized.

Subsequently, *Cryptococcus albidus* ATCC20293 is cultured, and after lyophilizing the resulting cells in liquid nitrogen, the cells are ground by using a mortar, etc., to obtain fine powder state cell pieces. Then, whole RNA fractions are extracted from the cell pieces by the conventional manner. In the extraction operation, a commercially available RNA kit can be utilized.

RNA is recovered from the resulting RNA extracted solution by ethanol precipitation, and RNA having a poly-A chain may be fractionated from the recovered RNA by the conventional manner. In the fractionation operation, a commercially available Oligo dT column can be utilized.

Next, by using the above obtained primer DNA based on a DNA sequence encoding a portion of the glutaminase, and the RNA obtained as mentioned above, DNAs containing fragments of the gene are amplified by a suitable RT-PCR reaction such as the 5' RACE method and the 3' RACE method, and these are ligated to obtain DNA containing whole gene. For a partial cDNA synthesis operation by the 5' RACE method or the 3' RACE method, a commercially available kit can be utilized.

DNA is amplified by carrying out PCR, using the above-mentioned cDNA as a template and using synthetic primers complementary to the 5'-terminus sequence and the 3'-terminus sequence. The amplified DNA can be cloned according to the conventional manner.

A recombinant DNA can be obtained by inserting the amplified DNA into a suitable vector. In the cloning, a commercially available kit such as TA Cloning Kit (trade name, available from Invitrogen Co.), a commercially available plasmid vector DNA such as pUC119 (trade name, available from Takara Shuzo Co.), pBR322 (trade name, available from Takara Shuzo Co.), pBluescript SK$^+$ (trade name, available from Stratagene Co.), and a commercially available bacteriophage vector DNA such as λEMBL3 (trade name, available from Stratagene Co.), etc. can be used.

By using the resulting recombinant DNA, a transformant or a transductant can be obtained respectively, by transforming or transducing, for example, *Escherichia coli* K-12, preferably *Escherichia coli* JM109 (trade name, available from Takara Shuzo Co.), XL-Blue (trade name, available from Funakoshi Co.), etc. Transformation can be carried out, for example, by the method of D. M. Morrison (Method in Enzymology, 68, pp. 326–331, 1979). Also, transduction can be carried out, for example, by the method of B. Hohn (Method in Enzymology, 68, pp. 299–309, 1979). As a host cell, in addition to *Escherichia coli*, other microorganism such as yeast, filamentous fungi, actinomycetes, etc., and animal cells can be used.

The whole or total base sequence (see SEQ ID NO:1) of the DNA amplified as mentioned above can be analyzed by using, for example, LI-COR MODEL 4200L sequencer (trade name, manufactured by LI-COR, Inc.), 370 DNA sequence system (trade name, manufactured by Perkin-Elmer Co.), and the like. By comparing the base sequence with information of a partial amino acid sequence, it can be confirmed whether a natural type glutaminase gene can be obtained or not.

From the analyses of the natural type glutaminase gene, translated polypeptide, i.e., an amino acid sequence of the protein as mentioned (a) can be determined.

2. Preparation Method of Glutaminase

When the glutaminase of the present invention is to be prepared, a recombinant DNA containing the glutaminase gene is firstly prepared. Then, a transformant or a transductant containing the recombinant DNA is prepared and cultured, and glutaminase is collected from a culture medium.

To produce the protein having a glutaminase activity by using the glutaminase gene of the present invention, it is necessary to select a suitable host-vector system. Such a system may include a system of yeast expression vector pYES2 (trade name, available from Invitrogen Co.) and yeast (*Saccharomyces cerevisiae*), a system of *Escherichia coli* expression vector pTE (trade name, available from Stratagene Co.) and *Escherichia coli* (*E. coli*) and the like. The system of yeast is preferably used in the point that sugar chain addition to the protein occurs.

The recombinant DNA can be obtained by inserting the glutaminase gene into a suitable vector. As the vector, there may be used, for example, yeast expression vector pYES2, pYD1 (both trade names, available from Invitrogen Co.), pAUR123 (trade name, available from Takara Shuzo, Co.), pYEX-BX, pYEX-S1, PYEX-4T (all trade names, available from CLONETECH Co.), YEpFLAG-1 (trade name, available from SIGMA Co.), *Escherichia coli* expression vector pSET (trade name, available from Invitrogen Co.), pTE (trade name, available from Stratagene Co.), and the like.

Then, the recombinant DNA is transformed or transduced in a host cell. Transformation into yeast can be carried out, for example, by the method of D. M. Becker et al. (Method in Enzymology, 194, 182–187, 1991). Transformation into *Escherichia coli* can be carried out, for example, by the above-mentioned method of D. M. MorrisonAs a host cell, microorganisms such as *Escherichia coli*, yeast, filamentous fungi, actinomycetes, etc., and animal cells can be used.

According to the above procedure, a transformant or a transductant having an ability of producing glutaminase can be obtained. To culture the transformant or the transductant, they may be cultured by the usual solid culture method, and a liquid culture method is preferably used if the situation allows.

When yeast is used as a host cell, as a medium, a generally employed nutrient-rich medium such as YPD medium and YM medium can be used. Also, when a selective medium is used depending on the genetic properties of the host cell, a SD medium which is the minimum medium can be used. When the selective medium is used, a selective pressure varies depending on the selected vector-host system so that an amino acid(s), a nucleic acid(s) and the like other than the selective pressure is/are added to the minimum medium depending on the genetic requirements of the host cell.

In addition, an inorganic salt(s), a starting material of sugar(s), vitamin(s) and the like may be optionally added to the medium, depending on necessity. Incidentally, an initial pH of the medium is preferably adjusted to pH 6 to 9. Moreover, some of the vectors can control expression of a protein. When these vectors are used, an inducer corresponding to the vector, such as galactose, a copper ion, etc., is added to the medium whereby glutaminase can be induced.

When yeast is cultured, culture is carried out at 25 to 35° C., preferably about 30° C. for 24 to 48 hours by an aeration stirring deep culture, shaking culture, standing culture, and the like.

Incidentally, the genetic engineering method in the present invention can be carried out, for example, according to the descriptions such as "Molecular Cloning: A Laboratory Manual 2nd Edition" (1989), Cold Spring Harbor Laboratory Press, ISBN 0-87969-309-6, "Current Protocols in Molecular Biology" (1989), John Wiley & Sons, Inc. ISBN 0-471-50338-X, etc.

EXAMPLES

In the following, Examples of the present invention will be explained more specifically, but the technical scope of the present invention is not limited by these.

Example 1

Cloning of Glutaminase Gene (1) Extraction of Chromosomal DNA from *Cryptococcus albidus*

*Cryptococcus albidus* ATCC20293 was cultured and after 1 g of the obtained microorganisms were frozen in liquid nitrogen, it was physically ground in a mortar to obtain cell particles in a fine powdery form. From this cell particles, genomic DNA was extracted by using a nucleic acid extracting reagent SepaGene (trade name, manufactured by Sanko Junyaku Co., Japan). The whole operation was carried out according to the protocol attached to the reagent.

(2) Determination of N-Terminal Amino Acid Sequences of Glutaminase

*Cryptococcus albidus* ATCC20293 was inoculated into a culture medium comprising 6.0% of glucose, 4% of corn steep liquor, 0.1% of $KH_2PO_4$ and 0.1% of $MgSO_4$ with a pH of 5.5, and cultured under shaking at 25° C. for 2 days to obtain a seed culture. 100 ml each of this seed culture was inoculated into 2 liters of the culture medium having the same composition as the above, and using 5 mini-jar, it was cultured at 25° C. for 3 days under condition of a stirring rate of 450 rpm and an aeration rate of 1 vvm, to obtain 10 liters of a culture broth containing the proliferated cells.

The culture broth containing the proliferated cells was subjected to centrifugal separation, and 50 g of the thus obtained microbial paste was collected, 500 ml of 0.2M acetate buffer (pH 5.0) was added thereto, and the cells were suspended well therein. Subsequently, as a cell wall lytic enzyme, 4 g of Cellulase Onozuka R-10 (trade name, manufactured by Yakult Honsha Co., Ltd.) was added thereto, and the resultant mixture was stirred at 42° C. for 18 hours, followed by a centrifugal separation (8,000 rpm, 20 minutes) to give a supernatant. The supernatant was heated at 60° C. for one hour, and after adjusting the pH to 6.8 by 0.2M $K_2HPO_4$, it was further heated at 60° C. for one hour to denature impure proteins and the thus denatured proteins were removed by centrifugation (8,000 rpm, 20 minutes).

To the above-mentioned supernatant was added ammonium sulfate to make the final concentration 1.2M, and the mixture was well stirred, and then, after kept at room temperature for one hour, it was subjected to centrifugation (8,000 rpm, 20 minutes) to remove insoluble proteins and obtain a crude enzyme solution. The above crude enzyme solution was applied to a Phenyl 5PW column ($\phi$ 21.5 mm×150 mm), and under the conditions of a current rate; 5 ml/min, a fractionating amount; 10 ml/fraction, a temperature; 25° C., a pressure; 30–42 $kg/cm^2$, and an eluent; solution A: 0.1M phosphate buffer containing 1.2M ammonium sulfate (pH 7.0), solution B: 0.1M phosphate buffer containing 20% ethylene glycol (pH 7.0), the enzyme was eluted with respective concentration gradients of from 1.2M to 0M ammonium sulfate and from 0% to 20% ethylene glycol (spending 75 minutes).

Subsequently, the active fraction(s) was/were concentrated by centriprep YM-10 (trade name, available from Amicon, Co.), and then, it was diluted by deionized water to lower the ionic strength of the active fractions. The fraction(s) was/were applied to a DEAE 5PW column (φ 7.5 mm×75 mm), and under the conditions of a current rate; 1 ml/min, a fractionating amount; 1 ml/fraction, a temperature; 25° C., a pressure; 8–12 kg/cm$^2$, and an eluent; solution A: 0.01M phosphate (pH 7.0), solution B: 0.01M phosphate buffer containing 1.0M NaCl (pH 7.0), the enzyme was eluted with a gradient concentration of from 0M to 1.0M of NaCl (spending 60 minutes).

The active fraction(s) was/were concentrated by centriprep YM-10 (trade name, available from Amicon, Co.), and then, it was applied to a Tsgel G3000 SW column (trade name, manufactured by Toyo Soda Co., φ 7.6 mm×600 mm×2), in an amount of 0.25 ml each, and eluted under the conditions of a current rate; 1 ml/min, a fractionating amount; 1 ml/fraction, a temperature; 25° C., a pressure; 74 kg/cm$^2$, and an eluent; 0.1M phosphate buffer containing 0.2M NaCl (pH 7.0). From an analysis of SDS-PAGE, the present enzyme was detected as a significantly broad main-band, and there were almost no impurity protein detected. This broad band also seemed to be two bands overlapped each other. However, almost the same results were obtained from 3 different modes of chromatographies, therefore, it was judged that a further purification was difficult, and the active fraction obtained at this stage was made the enzyme standard sample.

Bands for glycoproteins appear broad in SDS-PAGE. From that reason, decarbohydration treatment for removing sugars was carried out to confirm how far the enzyme was purified in terms of a simple protein.

5 μl of the purified enzyme solution was mixed with 4 μl of deionized water and 1 μl of X10 denatured buffer, and denaturing treatment was carried out at 100° C. for 10 minutes. Subsequently, to the treated solution were added 1.2 μl of X10 G7 Buffer, 1.2 μl of 10% NP-40 and 1 μl of PNGase F (500 U/μl), decarbohydration treatment was carried out at 37° C. for one hour. The obtained denaturing treatment solution was analyzed by SDS-PAGE. As a result, it was found out that there were 3 kinds of proteins with different sizes in the purified GLN sample. From this fact, it was shown that the glutaminase of Cryptococcus albidus was N-bond type glycosilated.

Subsequently, analyses on an N-terminus amino acid sequences of the above-mentioned 3 kinds of simple proteins were conducted. Analyses of primary amino acid sequence of the bands separated by SDS-PAGE were carried out by transferring the same to a PVDF membrane, followed by cutting out the membrane and applying this to Protein sequencer (Type 492, trade name, available from Applied Biosystem, Co.). Incidentally, for the transferring, a transferring device available from Nihon Eido Co. was used, and a method recommended by a Ministry of Agriculture and Fisheries was used while partially improving the same, by decreasing a concentration of methanol in a solution for blotting from 20% to 10%. Transferring was carried out at 40 mA for 90 minutes.

From the above-obtained information on analysis on the N-terminus amino acid sequence and information of the later-described DNA sequence of chromosomal DNA, it was assumed that N-terminus amino acid sequences of the 3 kinds of proteins were as shown in SEQ ID NO:3, 4 and 5.

Initially, from this result and the molecular weight of the enzyme obtained from a gel filtration method, it was assumed that glutaminase was a hetero trimer comprising three different subunits. Therefore, it was concerned that three kinds of proteins had to be separately cloned and since the total size of the gene is large, cloning of the gene is extremely difficult due to an instability of the gene itself even though the cloning is completed.

However, as described later, those fragments were derived from the same protein. It was concluded that these were the result of a partial digestion by a protease contained in the used cellulase, the result of a partial digestion by a protease existing in a purification process, or the result of difference in localization in vivo.

(3) Amplification of Partial Fragments of Glutaminase Gene by PCR Method

From the partial amino acid sequences of glutaminase determined in (2), primers represented by SEQ ID NO: 6 to 9 were designed and subjected to DNA syntheses.

That is, a sense mix primer represented by SEQ ID NO:6 corresponding to a peptide sequence represented by SEQ ID NO:3, a sense mix primer represented by SEQ ID NO:7 and an antisense mix primer represented by SEQ ID NO:8 corresponding to a peptide sequence represented by SEQ ID NO:4, and an antisense mix primer represented by SEQ ID NO:9 corresponding to a peptide sequence represented by SEQ ID NO:5 were synthesized, respectively. Using these primers, PCR reaction was carried out. For the reaction, Ex taq polymerase (trade name, manufactured by Takara Shuzo Co.) was used and conditions for the reaction mixture were set according to the protocol attached to the polymerase.

PCR reaction was carried out by Robocycler GRADIENT 96 (trade name, manufactured by Stratagene Co.). The basic reaction conditions were, for denature, 94° C. for 0.5 minute, for annealing, 37 to 46° C. for 0.5 minute and for elongation reaction, 72° C. for 2 minutes, those steps making one cycle, which was repeated for 40 cycles. The annealing temperature was gradually elevated from 37 to 46° C. with a temperature gradation.

Using the chromosomal DNA obtained in (1) as a template, there were detected amplifications of specific DNA fragments corresponding to about 350 bp in the PCR reaction combining the primer of SEQ ID NO:6 and the primer of SEQ ID NO:8, about 450 bp in the PCR reaction combining the primer of SEQ ID NO:6 and the primer of SEQ ID NO:9, and about 120 bp in the PCR reaction combining the primer of SEQ ID NO:7 and the primer of SEQ ID NO:9, respectively.

(4) Determination of DNA Sequence of the Amplified DNA Fragment

Each of the above-mentioned amplified DNA fragments was collected from a gel after 0.7% agarose gel electrophoresis, and this was inserted into a pCR2.1-TOPO vector using TOPO TA Cloning Kit (trade name, manufactured by Invitrogen Co.). The obtained recombinant plasmid was subjected to a sequence reaction using Thermo Sequenase Cycle Sequencing Kit (trade name, manufactured by Amersham Pharmacia Biotech Co.) and analyzed for its base sequence using LI-COR MODEL 4200L Sequencer (trade name, manufactured by LI-COR Co.). The sequence reaction was carried out according to the protocols attached to the materials.

As a result, in the amino acid sequence expected from the base sequence of the amplified fragment in the PCR reaction combining the primer of SEQ ID NO:7 and the primer of SEQ ID NO:9, there was identified a base sequence encoding amino acid residues not corresponding to the primer synthesis in the peptide sequence of SEQ ID NO:4 and SEQ ID NO:5. It was concluded from these facts that the amplified DNA fragment was a part of the gene encoding a target glutaminase.

Example 2

Preparation of Glutaminase cDNA (1) Extraction of Total RNA from *Cryptococcus albidus*

*Cryptococcus albidus* was inoculated into 100 ml of an YPD medium (2.0% of glucose, 1.0% of yeast extract and 2.0% of peptone), and cultured at 25° C. for 30 hours. After completion of culture, the resultant culture broth was centrifuged to collect the cells. About 500 mg of the cells among the resultant culture broth were frozen in liquid nitrogen and physically ground in a mortar to obtain cell particles in a powdery form. From the cell particles, total RNA was extracted using RNeasy Plant Mini Kit (trade name, manufactured by QIAGEN Co.). The whole operation was carried out according to the protocol attached to the Kit.

(2) Preparation of Glutaminase cDNA Using RACE Method

The above obtained total RNA was used to confirm amplification of about 1 kbp DNA fragment corresponding to 5'-terminal region of glutaminase cDNA and about 2 kbp DNA fragment corresponding to 3'-terminal region of glutaminase cDNA using First Choice RLM-RACE Kit (trade name, manufactured by Ambion Co.) and 3'-Full RACE Core Set (trade name, manufactured by Takara Shuzo Co.), respectively. The whole operation was carried out according to the protocols attached to the materials. Primers used for First Choice RLM-RACE Kit and for 3'-Full RACE Core Set were shown in SEQ ID NO:10 and 11, respectively. The thus amplified DNA fragments were cloned in the same manner as in Example 1-(4) to confirm their DNA sequences.

Then, using the information of the base sequence at 5' terminus of First Choice RLM-RACE Kit (trade name, Ambion Co.), a sense primer shown in SEQ ID NO:12 and complementary to 5' terminus base sequence of glutaminase cDNA was synthesized. Using the above 3'-Full RACE Core Set (trade name, manufactured by Takara Shuzo Co.), whole glutaminase cDNA was amplified (about 2.1 kbp) using a primer of SEQ ID NO:12 in place of a primer of SEQ ID NO:11, and a primer of SEQ ID NO:13 in place of an adapter primer attached to the kit.

The thus amplified DNA fragment was inserted into a pCR2.1-TOPO vector using TOPO TA Cloning Kit (trade name, manufactured by Invitrogen Co.) in the same manner as in Example 1-(4) to obtain a recombinant DNA (plasmid pCKgln).

From analysis on base sequence of the DNA fragment inserted into plasmid pCKgln, it was clarified that the DNA fragment contained glutaminase gene shown by the base numbers 1 to 2103 of SEQ ID NO:1. The base numbers 1 to 2100 of SEQ ID NO:1 represent a coding region and the base numbers 2101 to 2103 represent a stop codon. An amino acid sequence of a polypeptide translated from the glutaminase gene is shown in SEQ ID NO:2. In the amino acid sequence of the polypeptide translated from said DNA sequence, all of the N-terminus polypeptide sequences represented by SEQ ID NO:3 to 5 were identified. Incidentally, in SEQ ID NO:3, Gly at 12th and Gly at 16th were judged to be misreading by the device.

From these results, it was elucidated that three kinds of simple proteins contained in the purified standard product were formed by partial lysis of the same protein as stated above, and that glutaminase is not a trimer of different kinds of proteins as initially expected, but a trimer comprising proteins encoded in the same gene.

The plasmid pCKgln containing the whole glutaminase cDNA, that is, the base sequence represented by the base numbers 1 to 2013 of SEQ ID NO:1 is deposited as "FERM P-18308" with the National Institute of Advanced Industrial Science and Technology, Patent Microorganism Depository, Japan.

Example 3

Expression of Glutaminase cDNA

The above-mentioned plasmid pCKgln was digested enzymatically by the restriction enzymes EcoR I and Kpn I (both available from Takara Shuzo Co.), and then, it was applied to 0.7% agarose gel electrophoresis. DNA fragments contained in the gel corresponding to the target size (about 2 kbp) was cut out and purified. Subsequently, the above-obtained DNA fragment was inserted into a yeast expression vector pYES2 (trade name, manufactured by Invitrogen Co.) treated enzymatically with the same restriction enzymes to prepare a plasmid pYES-CKgln. By using the above plasmid, expression of the target protein (glutaminase) can be induced by galactose. As a host, INVSc1 available from Invitrogen Co. (genotype: MATa, his3Δ1, leu2, trp1-289, ura3-52/MATα, his3Δ1, leu2, trp1-289, ura3-52) was used. By the lithium acetate method, the host yeast was transformed by the above plasmid pYES-CKgln. As a selection medium, 0.67% Yeast Nitrogen base without amino acids (available from Difco Co.), 2% raffinose (available from Wako Junyaku Kogyo Co.), 0.01% adenine, arginine, cysteine, leucine, lysine, threonine, tryptophan, 0.005% aspartic acid, histidine, isoleucine, methionine, phenylalanine, proline, serine, tyrosine and valine (all available from Kanto Kagaku Co.) were used. The lithium acetate method was carried out according to the description in "Kaiser C. Michaelis S, Mitchell A: Lithium acetate yeast transformation, Methods in Yeast Genetics, A cold Spring harbor Laboratory Course Manual 1994 edition (Cold Spring Harbor Laboratory press, pp. 133–134, 1994)". Then, using the obtained transformant, protein was expressed according to the protocol attached to the pYES2 vector. The transformant obtained from a colony was inoculated in 20 ml of a selection medium in a 200 ml-volume baffled Erlenmeyer flask, and cultured under shaking at 30° C. at 140 rpm for about 14 hours to give seed culture. Turbidity ($OD_{600}$) of the seed culture was measured and the seed culture was inoculated into a protein expression inducing medium so that the initial turbidity was $OD_{600}$=0.4. A 500 ml-volume Sakaguchi flask was used for a culture by the protein expression inducing medium, and the seed culture was cultured under shaking in 50 ml of the medium at 30° C. at 140 rpm. For the protein expression inducing medium, 1% raffinose and 2% galactose (available from Wako Junyaku Kogyo Co.) were used as carbon sources in a selection medium.

Glutaminase activity was measured by partly modifying the method described in Japanese Provisional Patent Publication No. 332553/1999. That is, to 250 µl of 2% (w/v) L-glutamine solution were added 500 µl of 0.2M phosphate buffer (pH 6.5) and 250 µl of an enzyme solution, and the mixture was reacted at 37° C. for 30 minutes, and then, the reaction was terminated by adding 250 µl of 0.75N perchloric acid solution, and 125 µl of 1.5N sodium hydroxide solution was added thereto to neutralize the reaction mixture. The above reaction mixture was then centrifuged (10,000 rpm, 10 minutes). To 100 μl of the resultant supernatant were added 1.0 ml of 0.1M hydrochloric acid-hydroxylamine buffer (pH 8.0), 1.0 ml of 20 mM NAD+ solution (available from Oriental Yeast Co.) and 50 μl of 500 U/ml L-glutamate dehydrogenase solution (available from SIGMA Co.), and the mixture was reacted at 37° C. for 30 minutes and the absorbance at 340 nm was measured with a spectrophotometer. An amount of the enzyme forming 1 μmol of glutamic acid per one minute under the above conditions is determined as 1 unit (U).

It was shown that the transformant by the plasmid pYES-CKgln cultured in a protein expression inducing medium containing galactose had an increased glutaminase activity as compared to the transformant by the plasmid pYES2. It also exhibited an increased glutaminase activity when compared to the case where the trans formant by plasmid pYES-CKgln was cultured in a medium not containing galactose, without inducing protein expression.

The results from the measurements of enzyme activity of the above transformed yeast are shown in Table 1. The values in the table represent a glutaminase activity (mU/ml) per 1 ml of the culture broth after 24 hours of culture ($OD_{600}$=15). The term "vector" means a transformant by plasmid pYES2, "CK-GLN" means a transformant by plasmidpYES-CKgln. Additionally, (−) means the cells were cultured in a medium not containing galactose without inducing protein expression, and (+) means they were cultured in a protein expression inducing medium containing galactose.

Glutaminase activity of the transformant by plasmid pYES-CKgln was observed on the cell surface as in the case of *Cryptococcus albidus* G62 strain.

TABLE 1

| Vector (−) | Vector (+) | CK-GLN (−) | CK-GLN (+) |
|---|---|---|---|
| 0.63 | 0.66 | 2.59 | 25.50 |

From the above, it was clarified that the DNA represented by the base numbers 1 to 2100 of SEQ ID NO:1 is a glutaminase gene.

According to the present invention, there were provided a protein having a glutaminase activity and a glutaminase gene encoding the same. In addition, there were provided a recombinant DNA containing the glutaminase gene, and a transformed or transduced cell containing the recombinant DNA. Further, according to the present invention, there was provided a method for producing glutaminase comprising culturing the above transformed or transduced cell and collecting glutaminase from the culture product.

The glutaminase of the present invention has a significant effect on improving product quality in production of soy sauce and flavoring foods containing a large amount of salt. In addition, use of the glutaminase gene of the present invention enables a further modification of the function of the enzyme by means of genetic engineering method and constructing a method for mass production of this enzyme. It is concluded that the present invention is extremely useful in industry.

What is claimed is:

1. An isolated DNA comprising a sequence encoding the amino acid sequence of SEQ ID NO:2.

2. The DNA of claim 1, comprising the polynucleotide sequence of SEQ ID NO:1.

* * * * *